United States Patent
Van Dyke

(10) Patent No.: US 10,195,314 B2
(45) Date of Patent: Feb. 5, 2019

(54) FRACTIONATION OF CHARGED KERATIN

(71) Applicant: Wake Forest University Health Sciences, Winston-Salem, NC (US)

(72) Inventor: Mark E. Van Dyke, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 46 days.

(21) Appl. No.: 14/839,060

(22) Filed: Aug. 28, 2015

(65) Prior Publication Data

US 2015/0367043 A1     Dec. 24, 2015

Related U.S. Application Data

(62) Division of application No. 12/279,641, filed as application No. PCT/US2007/004193 on Feb. 15, 2007, now Pat. No. 9,149,566.

(60) Provisional application No. 60/774,587, filed on Feb. 17, 2006, provisional application No. 60/774,920, filed on Feb. 17, 2006, provisional application No. 60/774,442, filed on Feb. 17, 2006.

(51) Int. Cl.
| | | |
|---|---|---|
| C07K 1/36 | (2006.01) |
| C07K 14/47 | (2006.01) |
| A61L 33/12 | (2006.01) |
| A61L 15/32 | (2006.01) |
| A61L 26/00 | (2006.01) |
| A61L 27/22 | (2006.01) |
| A61L 27/34 | (2006.01) |
| A61L 29/04 | (2006.01) |
| A61L 29/08 | (2006.01) |
| A61L 31/04 | (2006.01) |
| A61L 31/10 | (2006.01) |
| A61K 38/17 | (2006.01) |
| A61L 27/54 | (2006.01) |
| A61L 29/16 | (2006.01) |
| A61L 31/16 | (2006.01) |
| A61L 33/00 | (2006.01) |

(52) U.S. Cl.
CPC ........ *A61L 33/128* (2013.01); *A61K 38/1748* (2013.01); *A61L 15/32* (2013.01); *A61L 26/0047* (2013.01); *A61L 27/227* (2013.01); *A61L 27/34* (2013.01); *A61L 27/54* (2013.01); *A61L 29/048* (2013.01); *A61L 29/085* (2013.01); *A61L 29/16* (2013.01); *A61L 31/047* (2013.01); *A61L 31/10* (2013.01); *A61L 31/16* (2013.01); *A61L 33/0041* (2013.01); *C07K 1/36* (2013.01); *C07K 14/4741* (2013.01); *A61L 2300/42* (2013.01); *A61L 2300/424* (2013.01)

(58) Field of Classification Search
None
See application file for complete search history.

(56) References Cited

PUBLICATIONS

Sayers et al.,"Structure and Assembly of Calf Hoof Keratin Filaments", Journal of Structural Biology 103: 212-224 (1990).*
MeSH database search of "kerateine" for alternative polypeptide names. Printed PDF results on Mar. 6, 2017.*
Nakamura et al. "A rapid extraction procedure of human hair proteins and identification of phosphorylated species", Biol. Pharm. Bull. 25(5): 569-572 (2002).*
Goddard and Michaelis, "A study of Keratin", J. Biol. Chem. 106: 605-614 (1934).*
PubMed printout of MeSH search for alpha keratin. Printout on Mar. 22, 2018. (Year: 2018).*
PubMed printout of MeSH search for gamma keratin. Printout on Mar. 22, 2018. (Year: 2018).*

* cited by examiner

*Primary Examiner* — Anand U Desai
(74) *Attorney, Agent, or Firm* — Myers Bigel, P.A.

(57) ABSTRACT

Methods are provided to produce optimal fractionations of charged keratins that have superior biomedical activity. Also provided are medical implants coated with these keratin preparations. Further provided are methods of treating blood coagulation in a patient in need thereof.

6 Claims, No Drawings

FRACTIONATION OF CHARGED KERATIN

RELATED APPLICATIONS

This application is a divisional of and claims priority to U.S. patent application Ser. No. 12/279,641, filed Sep. 2, 2008, which is a national phase application of PCT Application PCT/US2007/004193, filed Feb. 15, 2007, and published in English on Aug. 30, 2007, as International Publication No. WO 2007/098053, and which claims the benefit under 35 U.S.C. § 119(e) of U.S. Provisional Patent Application Ser. No. 60/774,442, filed Feb. 17, 2006, U.S. Provisional Patent Application Ser. No. 60/774,587, filed Feb. 17, 2006, and U.S. Provisional Patent Application Ser. No. 60/774,920, filed Feb. 17, 2006, the disclosures of each of which is incorporated herein by reference in its entirety.

This application is related to: Mark E. Van Dyke, U.S. patent application Ser. No. 11/205,800, titled: *Ambient Stored Blood Plasma Expanders*, filed Aug. 17, 2005, and published on Mar. 9, 2006, as 2006/0051732; Mark E. Van Dyke, U.S. patent application Ser. No. 11/673,212, titled: *Nerve Regeneration Employing Keratin Biomaterials*, filed Feb. 9, 2007, and published on Dec. 27, 2007, as 2007/0298070; and Mark E. Van Dyke, U.S. patent application Ser. No. 11/676,072, and PCT Application (published Aug. 30, 2007 as WO2007/098114), titled: *Clotting and Healing Compositions Containing Keratin Biomaterials*, filed Feb. 16, 2007.

GOVERNMENT SUPPORT

This invention was made with Government support under contract number W81XWH-04-1-0105 from the United States Army. The U.S. Government has certain rights to this invention.

FIELD OF THE INVENTION

The present invention is generally related to keratin biomaterials and the use thereof in biomedical applications.

BACKGROUND OF THE INVENTION

The earliest documented use of keratin in medicine comes from a Chinese herbalist named Li Shi-Zhen (Ben Cao Gang Mu. Materia Medica, a dictionary of Chinese herbs, written by Li Shi Zhen (1518-1593)). Over a 38-year period, he wrote a collection of 800 books known as the *Ben Cao Gang Mu*. These books were published in 1596, three years after his death. Among the more than 11,000 prescriptions described in these volumes, is a substance known as Xue Yu Tan, also known as Crinis Carbonisatus, that is made up of ground ash from pyrolized human hair. The stated indications for Xue Yu Tan were accelerated wound healing and blood clotting.

In the early 1800s, when proteins were still being called albuminoids (albumin was a well known protein at that time), many different kinds of proteins were being discovered. Around 1849, the word "keratin" appears in the literature to describe the material that made up hard tissues such as animal horns and hooves (keratin comes from the Greek "kera" meaning horn). This new protein intrigued scientists because it did not behave like other proteins. For example, the normal methods used for dissolving proteins were ineffective with keratin. Although methods such as burning and grinding had been known for some time, many scientists and inventors were more interested in dissolving hair and horns in order to make better products.

The resolution to this insolubility problem came from a trade more than 700 years old—the tanning industry. In the years preceding World War I, lime was applied to the manufacture of keratin gels. In a United States patent issued in 1905, John Hoffmeier described a process for extracting keratins from animal horns using lime (German Pat No. 184,915, Dec. 18, 1905). He then used the extracted keratins to make gels that could be strengthened by adding formaldehyde (formaldehyde "crosslinking" is a popular method of strengthening such gels and is still used today to "fix" tissues containing structural proteins like keratin and collagen).

During the years from 1905 to 1935, many methods were developed to extract keratins using oxidative and reductive chemistries (Breinl F and Baudisch O, Z physiol Chem 1907; 52:158-69; Neuberg C, U.S. Pat. No. 926,999, Jul. 6, 1909; Lissizin T, Biochem Bull 1915; 4:18-23; Zdenko S, Z physiol Chem 1924; 136:160-72; Lissizin T, Z physiol Chem 1928; 173:309-11). By the late 1920s many techniques had been developed for breaking down the structures of hair, horns, and hooves, but scientists were confused by the behavior of some of these purified proteins. Scientists soon concluded that many different forms of keratin were present in these extracts, and that the hair fiber must be a complex structure, not simply a strand of protein. In 1934, a key research paper was published that described different types of keratins, distinguished primarily by having different molecular weights (Goddard D R and Michaelis L, J Biol Chem 1934; 106:605-14). This seminal paper demonstrated that there were many different keratin homologs, and that each played a different role in the structure and function of the hair follicle.

It was during the years of World War II and immediately after that one of the most comprehensive research projects on the structure and chemistry of hair fibers was undertaken. Driven by the commercialization of synthetic fibers such as Nylon and polyester, Australian scientists were charged with protecting the country's huge wool industry. Synthetic fibers were seen as a threat to Australia's dominance in wool production, and the Council for Scientific and Industrial Research (later the Commonwealth Scientific and Industrial Research Organisation or CSIRO) established the Division of Protein Chemistry in 1940. The goal of this fundamental research was to better understand the structure and chemistry of fibers so that the potential applications of wool and keratins could be expanded.

CSIRO scientists developed many methods for the extraction, separation, and identification of keratins. In 1965, CSIRO scientist W. Gordon Crewther and his colleagues published the definitive text on the chemistry of keratins (Crewther W G et al., The Chemistry of Keratins. Anfinsen C B Jr et al., editors. Advances in Protein Chemistry 1965. Academic Press. New York: 191-346). This chapter in *Advances in Protein Chemistry* contained references to more than 640 published studies on keratins. Once scientists knew how to extract keratins from hair fibers, purify and characterize them, the number of derivative materials that could be produced with keratins grew exponentially. In the decade beginning in 1970, methods to form extracted keratins into powders, films, gels, coatings, fibers, and foams were being developed and published by several research groups throughout the world (Anker C A, U.S. Pat. No. 3,642,498, Feb. 15, 1972; Kawano Y and Okamoto S, Kagaku To Seibutsu 1975; 13(5):291-223; Okamoto S, Nippon Shokuhin Kogyo Gakkaishi 1977; 24(1):40-50). All of these methods made use of the oxidative and reductive chemistries developed decades earlier.

In 1982, Japanese scientists published the first study describing the use of a keratin coating on vascular grafts as a way to eliminate blood clotting (Noishiki Y et al., Kobunshi Ronbunshu 1982; 39(4):221-7), as well as experiments on the biocompatibility of keratins (Ito H et al., Kobunshi Ronbunshu 1982; 39(4):249-56). Soon thereafter in 1985, two researchers from the UK published a review article speculating on the prospect of using keratin as the building block for new biomaterials development (Jarman T and Light J, World Biotech Rep 1985; 1:505-12). In 1992, the development and testing of a host of keratin-based biomaterials was the subject of a doctoral thesis for French graduate student Isabelle Valherie (Valherie I and Gagnieu C. Chemical modifications of keratins: Preparation of biomaterials and study of their physical, physiochemical and biological properties. Doctoral thesis. Inst Natl Sci Appl Lyon, France 1992). Soon thereafter, Japanese scientists published a commentary in 1993 on the prominent position keratins could take at the forefront of biomaterials development (Various Authors, Kogyo Zairyo 1993; 41(15) Special issue 2:106-9).

Taken together, the aforementioned body of published work is illustrative of the unique chemical, physical, and biological properties of keratins. However, there remains a need to create optimal fractionations of keratins that have superior biomedical activity.

SUMMARY OF THE INVENTION

The invention provides methods of making charged (i.e. acidic and basic) keratins by separating one from the other, e.g., by chromatography, and optionally further processing or purifying the retained fraction or fractions. In some embodiments, the keratins fractionated based on acidity consist essentially of alpha keratoses, gamma keratoses, or mixtures thereof. In other embodiments, the keratins fractionated consist essentially of alpha kerateines, gamma kerateines, or mixtures thereof.

Another aspect of the present invention is an implantable biomedical device, comprising: a substrate and a keratin derivative on the substrate, wherein the keratin derivative is present in an amount effective to reduce cell and tissue adhesion to the substrate. In some embodiments the keratin derivative comprises, consists of or consists essentially of basic alpha keratose, basic gamma keratose, basic alpha kerateine, basic gamma kerateine, or combinations thereof.

A further aspect of the present invention is an implantable anti-adhesive tissue barrier, comprising: a solid, physiologically acceptable substrate; and a keratin derivative on the substrate. In some embodiments the keratin derivative comprises, consists of or consists essentially of basic alpha keratose, basic gamma keratose, basic alpha kerateine, basic gamma kerateine, or combinations thereof.

Yet another aspect of the present invention is a method of treating blood coagulation in a subject in need thereof, comprising administering a keratin derivative to said subject in an amount effective to inhibit blood coagulation in said subject, wherein said keratin derivative consists essentially of basic keratose, basic kerateine, or combinations thereof.

Another aspect of the present invention is the use of a keratin derivative as described herein for the preparation of a composition or medicament for carrying out a method of treatment as described herein, or for making an article of manufacture as described herein.

DETAILED DESCRIPTION OF THE PREFERRED EMBODIMENTS

The unique properties of subfamilies of keratins can be revealed and utilized through more sophisticated means of purification.

"Subjects" (or "patients") to be treated with the methods and compositions described herein include both human subjects and animal subjects (particularly other mammalian subjects such as dogs, cats, horses, monkeys, etc.) for veterinary purposes. Human subjects are particularly preferred. The subjects may be male or female and may be any age, including neonate, infant, juvenile, adolescent, adult, and geriatric subjects.

The disclosures of all United States patent references cited herein are to be incorporated herein by reference.

The ability of extracted keratin solutions to spontaneously self-assemble at the micron scale was published in two papers in 1986 and 1987 (Thomas H et al., Int J Biol Macromol 1986; 8:258-64; van de Locht M, Melliand Textilberichte 1987; 10:780-6). This phenomenon is not surprising given the highly controlled superstructure whence hair keratins are obtained. When processed correctly, this ability to self-assemble can be preserved and used to create regular architectures on a size scale conducive to cellular infiltration. When keratins are hydrolyzed (e.g., with acids or bases), their molecular weight is reduced and they lose the ability to self-assemble. Therefore, processing conditions that minimize hydrolysis are preferred.

This ability to self-assemble is a particularly useful characteristic for tissue engineering scaffolds for two reasons. First, self-assembly results in a highly regular structure with reproducible architectures, dimensionality, and porosity. Second, the fact that these architectures form of their own accord under benign conditions allows for the incorporation of cells as the matrix is formed. These two features are critically important to any system that attempts to mimic the native extracellular matrix (ECM).

Cellular recognition is also an important characteristic of biomaterials that seek to mimic the ECM. Such recognition is facilitated by the binding of cell surface integrins to specific amino acid motifs presented by the constituent ECM proteins. Predominant proteins include collagen and fibronectin, both of which have been extensively studied with regard to cell binding. Both proteins contain several regions that support attachment by a wide variety of cell types. It has been shown that in addition to the widely know Arginine-Glycine-Aspartic Acid (RGD) motif, the "X"-Aspartic Acid-"Y" motif on fibronectin is also recognized by the integrin $\alpha 4\beta 1$, where X equals Glycine, Leucine, or Glutamic Acid, and Y equals Serine or Valine. Keratin biomaterials derived from human hair contain these same binding motifs. A search of the NCBI protein database revealed sequences for 71 discrete, unique human hair keratin proteins. Of these, 55 are from the high molecular weight, low sulfur, alpha-helical family. This group of proteins is often referred to as the alpha-keratins and is responsible for imparting toughness to human hair fibers. These alpha-keratins have molecular weights greater than 40 kDa and an average cysteine (the main amino acid responsible for inter- and intramolecular protein bonding) content of 4.8 mole percent. Moreover, analysis of the amino acid sequences of these alpha keratin proteins showed that 78% contain at least one fibronectin-like integrin receptor binding motif, and 25% contain at least two or more. Two recent papers have highlighted the fact that these binding sites are likely present on the surface of keratin biomaterials by demonstrating excellent cell adhesion onto processed keratin foams (Tachibana A et al., J Biotech 2002; 93:165-70; Tachibana A et al., Biomaterials 2005; 26(3):297-302).

Other examples of natural polymers that may be utilized in a similar fashion to the disclosed keratin preparations include, but are not limited to, collagen, gelatin, fibronectin, vitronectin, laminin, fibrin, mucin, elastin, nidogen (entactin), proteoglycans, etc. (See, e.g., U.S. Pat. No. 5,691,203 to Katsuen et al.).

There are two theories for the biological activity of human hair extracts. The first is that the human hair keratins ("HHKs") themselves are biologically active. Over 70 human hair keratins are known and their cDNA-derived sequences published. However, the full compliment of HHKs is unknown and estimates of over 100 have been proposed (Gillespie J M, The structural proteins of hair: isolation characterization, and regulation of biosynthesis. Goldsmith L A (editor), Biochemistry and physiology of the skin (1983), Oxford University Press. New York; 475-510). Within the complete range of HHKs are a small number that have been shown to participate in wound contracture and cell migration (Martin, P, Science 1997; 276:75-81). In particular, keratins K-6 and K-16 are expressed in the epidermis during wound healing and are also found in the outer root sheath of the hair follicle (Bowden P E, Molecular Aspects of Dermatology (1993), John Wiley & Sons, Inc., Chichester: 19-54). The presence of these HHKs in extracts of human hair, and their subsequent dosing directly into a wound bed, may be responsible for "shortcutting" the otherwise lengthy process of differentiation, migration, and proliferation, or for alleviating some biochemical deficiency, thereby accelerating the tissue repair and regeneration process.

It has been known for more than a decade that growth factors such as bone morphogenetic protein-4 (BMP-4) and other members of the transforming growth factor-β (TGF-β) superfamily are present in developing hair follicles (Jones C M et al., Development 1991; 111:531-42; Lyons K M et al., Development 1990; 109:833-44; Blessings M et al., Genes and Develop 1993; 7:204-15). In fact, more than 30 growth factors and cytokines are involved in the growth of a cycling hair follicle (Hardy M H, Trends Genet 1992; 8(2):55-61; Stenn K S et al., J Dermato Sci 1994; 7S:S109-24; Rogers G E, Int J Dev Biol 2004; 48(2-3):163-70). Many of these molecules have a pivotal role in the regeneration of a variety of tissues. It is highly probable that a number of growth factors become entrained within human hair when cytokines bind to stem cells residing in the bulge region of the hair follicle (Panteleyev A A et al., J Cell Sci 2001; 114:3419-31). These growth factors would most certainly be extracted along with the keratins from end-cut human hair. This observation is not without precedent, as it has previously been shown that many different types of growth factors are present in the extracts of various tissues, and that their activity is maintained even after chemical extraction. Observations such as these show mounting evidence that a number of growth factors may be present in end-cut human hair, and that the keratins may be acting as a highly effective delivery matrix of, inter alia, these growth factors.

Keratins are a family of proteins found in the hair, skin, and other tissues of vertebrates. Hair is a unique source of human keratins because it is one of the few human tissues that is readily available and inexpensive. Although other sources of keratins are acceptable feedstocks for the present invention, (e.g. wool, fur, horns, hooves, beaks, feathers, scales, and the like), human hair is preferred for use with human subjects because of its biocompatibility.

Keratins can be extracted from human hair fibers by oxidation or reduction using methods that have been published in the art (See, e.g., Crewther W G et al. The chemistry of keratins, in Advances in protein chemistry 1965; 20:191-346). These methods typically employ a two-step process whereby the crosslinked structure of keratins is broken down by either oxidation or reduction. In these reactions, the disulfide bonds in cysteine amino acid residues are cleaved, rendering the keratins soluble (Scheme 1). The cuticle is essentially unaffected by this treatment, so the majority of the keratins remain trapped within the cuticle's protective structure. In order to extract these keratins, a second step using a denaturing solution must be employed. Alternatively, in the case of reduction reactions, these steps can be combined. Denaturing solutions known in the art include urea, transition metal hydroxides, surfactant solutions, and combinations thereof. Preferred methods use aqueous solutions of tris in concentrations between 0.1 and 1.0 M, and urea solutions between 0.1 and 10M, for oxidation and reduction reactions, respectively.

Scheme 1. General representations of (a) oxidation and (b) reduction of disulfide crosslinks in keratin. These reactions cleave the sulfur-sulfur bond in cystine residues, thereby destroying the superstructure and rendering the keratins soluble in the reaction media. The resultant fractions are keratose (a) and kerateine (b).

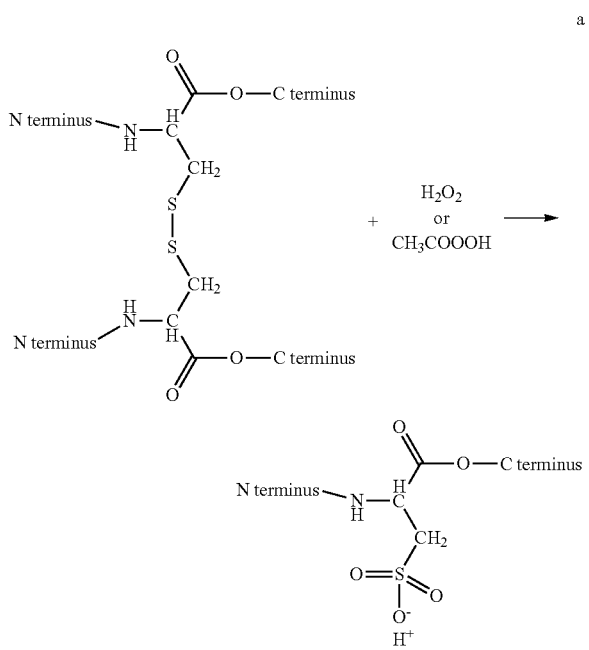

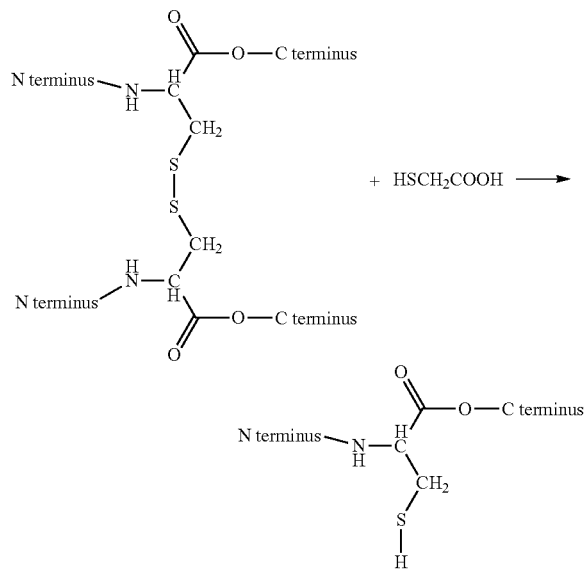

If one employs an oxidative treatment, the resulting keratins are referred to as "keratoses." If a reductive treatment is used, the resulting keratins are referred to as "kerateines" (See Scheme 1)

Crude extracts of keratins, regardless of redox state, can be further refined into "gamma" and "alpha" fractions, e.g., by isoelectric precipitation. High molecular weight keratins, or "alpha keratins," (alpha helical), are thought to derive from the microfibrillar regions of the hair follicle, and typically range in molecular weight from about 40-85 kiloDaltons. Low molecular weight keratins, or "gamma keratins," (globular), are thought to derive from the extracellular matrix regions of the hair follicle, and typically range in molecular weight from about 10-15 kiloDaltons. (See Crewther W G et al. The chemistry of keratins, in Advances in Protein Chemistry 1965; 20:191-346)

Even though alpha and gamma keratins possess unique properties, the properties of subfamilies of both alpha and gamma keratins can only be revealed through more sophisticated means of purification. For example, keratins may be fractionated into "acidic" and "basic" protein fractions. A preferred method of fractionation is ion exchange chromatography. These fractions possess unique properties, such as their differential effects on blood cell aggregation (See Table 1 below; See also: U.S. Patent Application Publication No. 2006/0051732).

"Keratin derivative" as used herein refers to any keratin fractionation, derivative, subfamily, etc., or mixtures thereof, alone or in combination with other keratin derivatives or other ingredients, including but not limited to alpha keratose, gamma keratose, alpha kerateine, gamma kerateine, meta keratin, keratin intermediate filaments, and combinations thereof, including the acidic and basic constituents thereof unless specified otherwise, along with variations thereof that will be apparent to persons skilled in the art in view of the present disclosure. In some embodiments, the keratin derivative comprises, consists or consists essentially of a particular fraction or subfraction of keratin. The derivative may comprise, consist or consist essentially of at least 80, 90, 95 or 99 percent by weight of said fraction or subfraction (or more).

In some embodiments, the keratin derivative comprises, consists of, or consists essentially of acidic alpha keratose.

In some embodiments, the keratin derivative comprises, consists of or consists essentially of alpha keratose, where the alpha keratose comprises, consists of or consists essentially of at least 80, 90, 95 or 99 percent by weight of acidic alpha keratose (or more), and where the alpha keratose comprises, consists of or consists essentially of not more than 20, 10, 5 or 1 percent by weight of basic alpha keratose (or less).

In some embodiments, the keratin derivative comprises, consists of, or consists essentially of basic alpha keratose.

In some embodiments, the keratin derivative comprises, consists of or consists essentially of alpha keratose, where the alpha keratose comprises, consists of or consists essentially of at least 80, 90, 95 or 99 percent by weight of basic alpha keratose (or more), and where the alpha keratose comprises, consists of or consists essentially of not more than 20, 10, 5 or 1 percent by weight of acidic alpha keratose (or less).

In some embodiments, the keratin derivative comprises, consists of, or consists essentially of acidic alpha kerateine.

In some embodiments, the keratin derivative comprises, consists of or consists essentially of alpha kerateine, where the alpha kerateine comprises, consists of or consists essentially of at least 80, 90, 95 or 99 percent by weight of acidic alpha kerateine (or more), and where the alpha kerateine comprises, consists of or consists essentially of not more than 20, 10, 5 or 1 percent by weight of basic alpha kerateine (or less).

In some embodiments, the keratin derivative comprises, consists of, or consists essentially of basic alpha kerateine.

In some embodiments, the keratin derivative comprises, consists of or consists essentially of alpha kerateine, where the alpha kerateine comprises, consists of or consists essentially of at least 80, 90, 95 or 99 percent by weight of basic alpha kerateine (or more), and where the alpha kerateine comprises, consists of or consists essentially of not more than 20, 10, 5 or 1 percent by weight of acidic alpha kerateine (or less).

In some embodiments, the keratin derivative comprises, consists of or consists essentially of unfractionated alpha+gamma-kerateines. In some embodiments, the keratin derivative comprises, consists of or consists essentially of acidic alpha+gamma-kerateines. In some embodiments, the keratin derivative comprises, consists of or consists essentially of basic alpha+gamma-kerateines.

In some embodiments, the keratin derivative comprises, consists of or consists essentially of unfractionated alpha+gamma-keratose. In some embodiments, the keratin derivative comprises, consists of or consists essentially of acidic alpha+gamma-keratose. In some embodiments, the keratin derivative comprises, consists of or consists essentially of basic alpha+gamma-keratose.

In some embodiments, the keratin derivative comprises, consists of or consists essentially of unfractionated beta-keratose (e.g., derived from cuticle). In some embodiments, the keratin derivative comprises, consists of or consists essentially of basic beta-keratose. In some embodiments, the keratin derivative comprises, consists of or consists essentially of acidic beta-keratose.

The basic alpha keratose is preferably produced by separating basic alpha keratose from a mixture comprising acidic and basic alpha keratose, e.g., by ion exchange chromatography, and optionally the basic alpha keratose has an average molecular weight of from 10 to 100 or 200 kiloDaltons. More preferably, the average molecular weight is from 30 or 40 to 90 or 100 kiloDaltons. Optionally but preferably the process further comprises the steps of re-disolving said basic alpha-keratose in a denaturing and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of acidic alpha keratose, or less.

The acidic alpha keratose is preferably produced by a reciprocal of the foregoing technique: that is, by separating and retaining acidic alpha keratose from a mixture of acidic and basic alpha keratose, e.g., by ion exchange chromatography, and optionally the acidic alpha keratose has an average molecular weight of from 10 to 100 or 200 kiloDaltons. More preferably, the average molecular weight is from 30 or 40 to 90 or 100 kiloDaltons. Optionally but preferably the process further comprises the steps of re-dissolving said acidic alpha-keratose in a denaturing solution and/or buffering solution, optionally in the presence of a chelating agent to complex trace metals, and then re-precipitating the basic alpha keratose from the denaturing solution. It will be appreciated that the composition preferably contains not more than 5, 2, 1, or 0.1 percent by weight of basic alpha keratose, or less.

Basic and acidic fractions of other keratoses can be prepared in like manner as described above for basic and acidic alpha keratose.

The basic alpha kerateine is preferably produced by separating basic alpha kerateine from a mixture of acidic and basic alpha kerateine, e.g., by ion exchange chromatography, and optionally the basic alpha kerateine has an average molecular weight of from 10 to 100 or 200 kiloDaltons. More preferably, the average molecular weight is from 30 or 40 to 90 or 100 kiloDaltons. Optionally but preferably the process further comprises the steps of re-dissolving said basic alpha-kerateine in a denaturing and/or buffering solution, optionally in the presence of a chelating agent to complex trace metals, and then re-precipitating the basic alpha kerateine from the denaturing solution. It will be appreciated that the composition preferably contains not more than 5, 2, 1, or 0.1 percent by weight of acidic alpha kerateine, or less.

The acidic alpha kerateine is preferably produced by a reciprocal of the foregoing technique: that is, by separating and retaining acidic alpha kerateine from a mixture of acidic and basic alpha kerateine, e.g., by ion exchange chromatography, and optionally the acidic alpha kerateine has an average molecular weight of from 10 to 100 or 200 kiloDaltons. Optionally but preferably the process further comprises the steps of re-dissolving said acidic alpha-kerateine in a denaturing and/or buffering solution), optionally in the presence of a chelating agent to complex trace metals, and then re-precipitating the basic alpha kerateine from the denaturing solution. It will be appreciated that the composition preferably contains not more than 5, 2, 1, or 0.1 percent by weight of basic alpha kerateine, or less.

Basic and acidic fractions of other kerateines can be prepared in like manner as described above for basic and acidic alpha kerateine.

Keratin materials are derived from any suitable source, including, but not limited to, wool and human hair. In one embodiment keratin is derived from end-cut human hair, obtained from barbershops and salons. The material is washed in hot water and mild detergent, dried, and extracted with a nonpolar organic solvent (typically hexane or ether) to remove residual oil prior to use.

Keratoses. Keratose fractions are obtained by any suitable technique. In one embodiment they are obtained using the method of Alexander and coworkers (P. Alexander et al., *Biochem. J* 46, 27-32 (1950)). Basically, the hair is reacted with an aqueous solution of peracetic acid at concentrations of less than ten percent at room temperature for 24 hours. The solution is filtered and the alpha-keratose fraction precipitated by addition of mineral acid to a pH of approximately 4. The alpha-keratose is separated by filtration, washed with additional acid, followed by dehydration with alcohol, and then freeze dried. Increased purity can be achieved by redissolving the keratose in a denaturing solution such as 7M urea, aqueous ammonium hydroxide solution, or 20 mM tris base buffer solution (e.g., Trizma® base), re-precipitating, re-dissolving, dialyzing against deionized water, and re-precipitating at pH 4.

A preferred method for the production of keratoses is by oxidation with hydrogen peroxide, peracetic acid, or performic acid. A most preferred oxidant is peracetic acid. Preferred concentrations range from 1 to 10 weight/volume percent (w/v %), the most preferred being approximately 2 w/v %. Those skilled in the art will recognize that slight modifications to the concentration can be made to effect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peractic acid offers the advantages of cost and availability. A preferred oxidation temperature is between 0 and 100 degrees Celsius (° C.). A most preferred oxidation temperature is 37° C. A preferred oxidation time is between 0.5 and 24 hours. A most preferred oxidation time is 12 hours. A preferred liquid to solid ratio is from 5 to 100:1. A most preferred ratio is 20:1. After oxidation, the hair is rinsed free of residual oxidant using a copious amount of distilled water.

The keratoses can be extracted from the oxidized hair using an aqueous solution of a denaturing agent. Protein denaturants are well known in the art, but preferred solutions include urea, transition metal hydroxides (e.g. sodium and potassium hydroxide), ammonium hydroxide, and tris(hydroxymethyl)aminomethane (tris base). A preferred solution is Trizma® base (a brand of tris base) in the concentration range from 0.01 to 1M. A most preferred concentration is 0.1M. Those skilled in the art will recognize that slight modifications to the concentration can be made to effect varying degrees of extraction, with concomitant alterations in reaction time, temperature, and liquid to solid ratio. A preferred extraction temperature is between 0 and 100 degrees Celsius. A most preferred extraction temperature is 37° C. A preferred extraction time is between 0.5 and 24 hours. A most preferred extraction time is 3 hours. A preferred liquid to solid ratio is from 5 to 100:1. A most preferred ratio is 40:1. Additional yield can be achieved with subsequent extractions with dilute solutions of tris base or deionized (DI) water. After extraction, the residual solids are removed from solution by centrifugation and/or filtration.

The crude extract can be isolated by first neutralizing the solution to a pH between 7.0 and 7.4. A most preferred pH is 7.4. Residual denaturing agent is removed by dialysis against DI water. Concentration of the dialysis retentate is followed by lyophilization or spray drying, resulting in a dry powder mixture of both gamma- and alpha-keratose. Alternately, alpha-keratose is isolated from the extract solution by dropwise addition of acid until the pH of the solution reaches approximately 4.2. Preferred acids include sulfuric, hydrochloric, and acetic. A most preferred acid is concentrated hydrochloric acid. Precipitation of the alpha fraction begins at around pH 6.0 and continues until approximately 4.2. Fractional precipitation can be utilized to isolate different ranges of protein with different isoelectric properties. Solid alpha-keratose can be recovered by centrifugation or filtration.

The alpha keratose can be further purified by re-dissolving the solids in a denaturing solution. The same denaturing solutions as those utilized for extraction can be used, however a preferred denaturing solution is tris base. Ethylene diamine tetraacetic acid (EDTA) can be added to complex and remove trace metals found in the hair. A preferred denaturing solution is 20 mM tris base with 20 mM EDTA or DI water with 20 mM EDTA. If the presence of trace metals is not detrimental to the intended application, the EDTA can be omitted. The alpha-keratose is re-precipitated from this solution by dropwise addition of hydrochloric acid to a final pH of approximately 4.2. Isolation of the solid is by centrifugation or filtration. This process can be repeated several times to further purify the alpha-keratose.

The gamma keratose fraction remains in solution at pH 4 and is isolated by addition to a water-miscible organic solvent such as alcohol, followed by filtration, dehydrated with additional alcohol, and freeze dried. Increased purity can be achieved by re-dissolving the keratose in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and re-precipitating by addition to alcohol. The amount of alcohol consumed in these steps can be minimized by first concentrating the keratose solution by distillation.

After removal of the alpha keratose, the concentration of gamma keratose from a typical extraction solution is approximately 1-2%. The gamma keratose fraction can be isolated by addition to a water-miscible non-solvent. To effect precipitation, the gamma-keratose solution can be concentrated by evaporation of excess water. This solution can be concentrated to approximately 10-20% by removal of 90% of the water. This can be done using vacuum distillation or by falling film evaporation. After concentration, the gamma-keratose solution is added dropwise to an excess of cold non-solvent. Suitable non-solvents include ethanol, methanol, acetone, and the like. A most preferred non-solvent is ethanol. A most preferred method is to concentrate the gamma keratose solution to approximately 10 w/v % protein and add it dropwise to an 8-fold excess of cold ethanol. The precipitated gamma keratose can be isolated by centrifugation or filtration and dried. Suitable methods for drying include freeze drying (lyophilization), air drying, vacuum drying, or spray drying. A most preferred method is freeze drying.

Kerateines. Kerateine fractions can be obtained using a combination of the methods of Bradbury and Chapman (J. Bradbury et al., *Aust. J. Biol. Sci.* 17, 960-72 (1964)) and Goddard and Michaelis (D. Goddard et al., *J. Biol. Chem.* 106, 605-14 (1934)). Essentially, the cuticle of the hair fibers is removed ultrasonically in order to avoid excessive hydrolysis and allow efficient reduction of cortical disulfide bonds in a second step. The hair is placed in a solution of dichloroacetic acid and subjected to treatment with an ultrasonic probe. Further refinements of this method indicate that conditions using 80% dichloroacetic acid, solid to liquid of 1:16, and an ultrasonic power of 180 Watts are optimal (H. Ando et al., *Sen'i Gakkaishi* 31(3), T81-85 (1975)). Solid fragments are removed from solution by filtration, rinsed and air dried, followed by sieving to isolate the hair fibers from removed cuticle cells.

In some embodiments, following ultrasonic removal of the cuticle, alpha- and gamma-kerateines are obtained by reaction of the denuded fibers with mercaptoethanol. Specifically, a low hydrolysis method is used at acidic pH (E. Thompson et al., *Aust. J. Biol. Sci.* 15, 757-68 (1962)). In a typical reaction, hair is extracted for 24 hours with 4M mercaptoethanol that has been adjusted to pH 5 by addition of a small amount of potassium hydroxide in deoxygenated water containing 0.02M acetate buffer and 0.001 M surfactant.

The solution is filtered and the alpha-kerateine fraction precipitated by addition of mineral acid to a pH of approximately 4. The alpha-kerateine is separated by filtration, washed with additional acid, followed by dehydration with alcohol, and then dried under vacuum. Increased purity is achieved by re-dissolving the kerateine in a denaturing solution such as 7M urea, aqueous ammonium hydroxide solution, or 20 mM tris buffer solution, re-precipitating, re-dissolving, dialyzing against deionized water, and re-precipitating at pH 4.

The gamma kerateine fraction remains in solution at pH 4 and is isolated by addition to a water-miscible organic solvent such as alcohol, followed by filtration, dehydrated with additional alcohol, and dried under vacuum. Increased purity can be achieved by re-dissolving the kerateine in a denaturing solution such as 7M urea, aqueous ammonium hydroxide solution, or 20 mM tris buffer solution, reducing the pH to 4 by addition of a mineral acid, removing any solids that form, neutralizing the supernatant, re-precipitating the protein with alcohol, re-dissolving, dialyzing against deionized water, and reprecipitating by addition to alcohol. The amount of alcohol consumed in these steps can be minimized by first concentrating the keratin solution by distillation.

In an alternate method, the kerateine fractions are obtained by reacting the hair with an aqueous solution of sodium thioglycolate.

A preferred method for the production of kerateines is by reduction of the hair with thioglycolic acid or beta-mercaptoethanol. A most preferred reductant is thioglycolic acid (TGA). Preferred concentrations range from 1 to 10M, the most preferred being approximately 1.0M. Those skilled in the art will recognize that slight modifications to the concentration can be made to effect varying degrees of reduction, with concomitant alterations in pH, reaction time, temperature, and liquid to solid ratio. A preferred pH is between 9 and 11. A most preferred pH is 10.2. The pH of the reduction solution is altered by addition of base. Preferred bases include transition metal hydroxides, sodium hydroxide, and ammonium hydroxide. A most preferred base is sodium hydroxide. The pH adjustment is effected by dropwise addition of a saturated solution of sodium hydroxide in water to the reductant solution. A preferred reduction temperature is between 0 and 100° C. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1. Unlike the previously described oxidation reaction, reduction is carried out at basic pH. That being the case, keratins are highly soluble in the reduction media and are expected to be extracted. The reduction solution is therefore combined with the subsequent extraction solutions and processed accordingly.

Reduced keratins are not as hydrophilic as their oxidized counterparts. As such, reduced hair fibers will not swell and split open as will oxidized hair, resulting in relatively lower yields. Another factor affecting the kinetics of the reduction/extraction process is the relative solubility of kerateines. The relative solubility rankings in water is gamma-keratose>alpha-keratose>gamma-kerateine>alpha-kerateine from most to least soluble. Consequently, extraction yields from reduced hair fibers are not as high. This being the case, subsequent extractions are conducted with additional reductant plus denaturing agent solutions. Preferred solutions for subsequent extractions include TGA plus urea, TGA plus tris base, or TGA plus sodium hydroxide. After extraction, crude fractions of alpha- and gamma-kerateine can be isolated using the procedures described for keratoses. However, precipitates of gamma- and alpha-kerateine re-form their cystine crosslinks upon exposure to oxygen. Precipitates must therefore be re-dissolved quickly to avoid insolubility during the purification stages, or precipitated in the absence of oxygen.

Residual reductant and denaturing agents can be removed from solution by dialysis. Typical dialysis conditions are 1 to 2% solution of kerateines dialyzed against DI water for 24 to 72 hours. Those skilled in the art will recognize that other methods exist for the removal of low molecular weight contaminants in addition to dialysis (e.g. microfiltration, chromatography, and the like). The use of tris base is only required for initial solubilization of the kerateines. Once dissolved, the kerateines are stable in solution without the denaturing agent. Therefore, the denaturing agent can be removed without the resultant precipitation of kerateines, so long as the pH remains at or above neutrality. The final concentration of kerateines in these purified solutions can be adjusted by the addition/removal of water.

Regardless of the form of the keratin (i.e. keratoses or kerateines), several different approaches to further purification can be employed to keratin solutions. Care must be taken, however, to choose techniques that lend themselves to keratin's unique solubility characteristics. One of the most simple separation technologies is isoelectric precipitation. In this method, proteins of differing isoelectric point can be isolated by adjusting the pH of the solution and removing the precipitated material. In the case of keratins, both gamma- and alpha-forms are soluble at pH>6.0. As the pH falls below 6, however, alpha-keratins begin to precipitate. Keratin fractions can be isolated by stopping the precipitation at a given pH and separating the precipitate by centrifugation and/or filtration. At a pH of approximately 4.2, essentially all of the alpha-keratin will have been precipitated. These separate fractions can be re-dissolved in water at neutral pH, dialyzed, concentrated, and reduced to powders by lyophilization or spray drying. However, kerateine fractions must be stored in the absence of oxygen or in dilute solution to avoid crosslinking.

Another general method for separating keratins is by chromatography. Several types of chromatography can be employed to fractionate keratin solutions including size exclusion or gel filtration chromatography, affinity chromatography, isoelectric focusing, gel electrophoresis, ion exchange chromatography, and immunoaffinity chromatography. These techniques are well known in the art and are capable of separating compounds, including proteins, by the characteristics of molecular weight, chemical functionality, isoelectric point, charge, or interactions with specific antibodies, and can be used alone or in any combination to effect high degrees of separation and resulting purity.

A preferred purification method is ion exchange (IEx) chromatography. IEx chromatography is particularly suited to protein separation owning to the amphiphilic nature of proteins in general and keratins in particular. Depending on the starting pH of the solution, and the desired fraction slated for retention, either cationic or anionic IEx (CIEx or AIEx, respectively) techniques can be used. For example, at a pH of 6 and above, both gamma- and alpha-keratins are soluble and above their isoelectric points. As such, they are anionic and can be bound to an anionic exchange resin. However, it has been discovered that a sub-fraction of keratins does not bind to a weakly anionic exchange resin and instead passes through a column packed with such resin. A preferred solution for AIEx chromatography is purified or fractionated keratin, isolated as described previously, in purified water at a concentration between 0 and 5 weight/volume %. A preferred concentration is between 0 and 4 w/v %. A most preferred concentration is approximately 2 w/v %. It is preferred to keep the ionic strength of said solution initially quite low to facilitate binding to the AIEx column. This is achieved by using a minimal amount of acid to titrate a purified water solution of the keratin to between pH 6 and 7. A most preferred pH is 6. This solution can be loaded onto an AIEx column such as DEAE-Sepharose® resin or Q-Sepharose® resin columns. A preferred column resin is DEAE-Sepharose® resin. The solution that passes through the column can be collected and further processed as described previously to isolate a fraction of acidic keratin powder.

In some embodiments the activity of the keratin matrix is enhanced by using an AIEx column to produce the keratin that may be useful for, inter alia, promoting cell adhesion. Without wishing to be bound to any particular theory, it is envisioned that the fraction that passes through an anionic column, i.e. acidic keratin, promotes cell adhesion.

Another fraction binds readily, and can be washed off the column using salting techniques known in the art. A preferred elution medium is sodium chloride solution. A preferred concentration of sodium chloride is between 0.1 and 2M. A most preferred concentration is 2M. The pH of the solution is preferred to be between 6 and 12. A most preferred pH is 12. In order to maintain stable pH during the elution process, a buffer salt can be added. A preferred buffer salt is Trizma® base. Those skilled in the art will recognize that slight modifications to the salt concentration and pH can be made to effect the elution of keratin fractions with differing properties. It is also possible to use different salt concentrations and pH's in sequence, or employ the use of salt and/or pH gradients to produce different fractions. Regardless of the approach taken, however, the column eluent can be collected and further processed as described previously to isolate fractions of basic keratin powders.

A complimentary procedure is also feasible using CIEx techniques. Namely, the keratin solution can be added to a cation exchange resin such as SP Sepharose® resin (strongly cationic) or CM Sepharose® resin (weakly cationic), and the basic fraction collected with the pass through. The retained acid keratin fraction can be isolated by salting as previously described.

Meta Keratins. Meta keratins are synthesized from both the alpha and gamma fractions of kerateine using substantially the same procedures. Basically, the kerateine is dissolved in a denaturing solution such as 7M urea, aqueous ammonium hydroxide solution, or 20 mM tris buffer solution. Pure oxygen is bubbled through the solution to initiate oxidative coupling reactions of cysteine groups. The progress of the reaction is monitored by an increase in molecular weight as measured using SDS-PAGE. Oxygen is continually bubbled through the reaction solution until a doubling or tripling of molecular weight is achieved. The pH of the denaturing solution can be adjusted to neutrality to avoid hydrolysis of the proteins by addition of mineral acid.

Keratin Intermediate Filaments. IFs of human hair fibers are obtained using the method of Thomas and coworkers (H. Thomas et al., *Int. J. Biol. Macromol.* 8, 258-64 (1986)). This is essentially a chemical etching method that reacts away the keratin matrix that serves to "glue" the IFs in place, thereby leaving the IFs behind. In a typical extraction process, swelling of the cuticle and sulfitolysis of matrix proteins is achieved using 0.2M $Na_2SO_3$, 0.1M $Na_2O_6S_4$ in 8M urea and 0.1M Tris-HCl buffer at pH 9. The extraction proceeds at room temperature for 24 hours. After concentrating, the dissolved matrix keratins and IFs are precipitated by addition of zinc acetate solution to a pH of approximately 6. The IFs are then separated from the matrix keratins by dialysis against 0.05M tetraborate solution. Increased purity is obtained by precipitating the dialyzed solution with zinc acetate, redissolving the IFs in sodium citrate, dialyzing against distilled water, and then freeze drying the sample.

Further discussion of keratin preparations are found in U.S. Patent Application Publication 2006/0051732 (Van Dyke), which is incorporated by reference herein.

Formulations. Dry powders may be formed of keratin derivatives as described above in accordance with known techniques such as freeze drying (lyophilization). In some embodiments, compositions of the invention may be produced by mixing such a dry powder composition form with an aqueous solution to produce a composition comprising an electrolyte solution having said keratin derivative solubilized therein. The mixing step can be carried out at any suitable temperature, typically room temperature, and can be carried out by any suitable technique such as stirring, shaking, agitation, etc. The salts and other constituent ingredients of the electrolyte solution (e.g., all ingredients except the keratin derivative and the water) may be contained entirely in the dry powder, entirely within the aqueous composition, or may be distributed between the dry powder and the aqueous composition. For example, in some embodiments, at least a portion of the constituents of the electrolyte solution is contained in the dry powder.

The formation of a matrix comprising keratin materials such as described above can be carried out in accordance with techniques long established in the field or variations thereof that will be apparent to those skilled in the art. In some embodiments, the keratin preparation is dried and rehydrated prior to use. See, e.g., U.S. Pat. No. 2,413,983 to Lustig et al., U.S. Pat. No. 2,236,921 to Schollkipf et al., and U.S. Pat. No. 3,464,825 to Anker. In preferred embodiments, the matrix, or hydrogel, is formed by re-hydration of the lyophilized material with a suitable solvent, such as water or phosphate buffered saline (PBS). The gel can be sterilized, e.g., by γ-irradiation (800 krad) using a Co60 source. Other suitable methods of forming keratin matrices include, but are not limited to, those found in U.S. Pat. No. 6,270,793 (Van Dyke et al.), U.S. Pat. No. 6,274,155 (Van Dyke et al.), U.S. Pat. No. 6,316,598 (Van Dyke et al.), U.S. Pat. No. 6,461,628 (Blanchard et al.), U.S. Pat. No. 6,544,548 (Siller-Jackson et al.), and U.S. Pat. No. 7,01,987 (Van Dyke).

In some composition embodiments, the keratin derivatives (particularly alpha and/or gamma kerateine and alpha and/or gamma keratose) have an average molecular weight of from about 10 to 70 or 85 or 100 kiloDaltons. Other keratin derivatives, particularly meta-keratins, may have higher average molecular weights, e.g., up to 200 or 300 kiloDaltons. In general, the keratin derivative (this term including combinations of derivatives) may be included in the composition in an amount of from about 0.1, 0.5 or 1 percent by weight up to 3, 4, 5, or 10 percent by weight. The composition when mixed preferably has a viscosity of about 1 or 1.5 to 4, 8, 10 or 20 centipoise. Viscosity at any concentration can be modulated by changing the ratio of alpha to gamma keratose.

The keratin derivative composition or formulation may optionally contain one or more active ingredients such as one or more growth factors (e.g., in an amount ranging from 0.0000001 to 1 or 5 percent by weight of the composition that comprises the keratin derivative(s)) to facilitate growth or healing, facilitate or inhibit coagulation, facilitate or inhibit cell or tissue adhesion, etc. Examples of suitable active ingredients include but are not limited to nerve growth factor, vascular endothelial growth factor, fibronectin, fibrin, laminin, acidic and basic fibroblast growth factors, testosterone, ganglioside GM-1, catalase, insulin-like growth factor-I (IGF-I), platelet-derived growth factor (PDGF), neuronal growth factor galectin-1, and combinations thereof. See, e.g., U.S. Pat. No. 6,506,727 to Hansson et al. and U.S. Pat. No. 6,890,531 to Horie et al.

As used herein, "growth factors" include molecules that promote the regeneration, growth and survival of tissue. Growth factors that are used in some embodiments of the present invention may be those naturally found in keratin extracts, or may be in the form of an additive, added to the keratin extracts or formed keratin matrices. Examples of growth factors include, but are not limited to, nerve growth factor (NGF) and other neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), epidermal growth factor (EGF), hepatocyte growth factor (HGF), granulocyte-colony stimulating factor (G-CSF), and granulocyte-macrophage colony stimulating factor (GM-CSF). There are many structurally and evolutionarily related proteins that make up large families of growth factors, and there are numerous growth factor families, e.g., the neurotrophins (NGF, BDNF, and NT3). The neurotrophins are a family of molecules that promote the growth and survival of, inter alia, nervous tissue. Examples of neurotrophins include, but are not limited to, nerve growth factor (NGF), brain-derived neurotrophic factor (BDNF), neurotrophin 3 (NT-3), and neurotrophin 4 (NT-4). See U.S. Pat. No. 5,843,914 to Johnson, Jr. et al.; U.S. Pat. No. 5,488,099 to Persson et al.; U.S. Pat. No. 5,438,121 to Barde et al.; U.S. Pat. No. 5,235,043 to Collins et al.; and U.S. Pat. No. 6,005,081 to Burton et al.

For example, nerve growth factor (NGF) can be added to the keratin matrix composition in an amount effective to promote the regeneration, growth and survival of various tissues. The NGF is provided in concentrations ranging from 0.1 ng/mL to 1000 ng/mL. More preferably, NGF is provided in concentrations ranging from 1 ng/mL to 100 ng/mL, and most preferably 10 ng/mL to 100 ng/mL. See U.S. Pat. No. 6,063,757 to Urso.

Other examples of natural polymers that may be prepared and utilized in a similar fashion to the disclosed keratin preparations include, but are not limited to, collagen, gelatin, fibronectin, vitronectin and laminin (See, e.g., U.S. Pat. No. 5,691,203 to Katsuen et al.), with the necessary modifications apparent to those skilled in the art.

The composition is preferably sterile and non-pryogenic. The composition may be provided preformed and aseptically packaged in a suitable container, such as a flexible polymeric bag or bottle, or a foil container, or may be provided as a kit of sterile dry powder in one container and sterile aqueous solution in a separate container for mixing just prior to use. When provided pre-formed and packaged in a sterile container the composition preferably has a shelf life of at least 4 or 6 months (up to 2 or 3 years or more) at room temperature, prior to substantial loss of viscosity (e.g., more than 10 or 20 percent) and/or substantial precipitation of the keratin derivative (e.g., settling detectable upon visual inspection).

Coatings and Biomedical Implants. As noted above, the present invention provides an implantable biomedical device, comprising: a substrate and a keratin derivative on the substrate, wherein the keratin derivative is present in an amount effective to reduce cell and/or tissue adhesion to the substrate. In some embodiments the keratin derivative comprises, consists of or consists essentially of basic alpha keratose, basic alpha kerateine, or combinations thereof.

The chemistry of keratins can be utilized to optimize the properties of keratin-based coatings. Alpha and gamma keratoses have inert sulfur residues. The oxidation reaction is a terminal step and results in the conversion of cystine residues into two non-reactive sulfonic acid residues. Kerateines, on the other hand, have labile sulfur residues. During the creation of the kerateines, cystine is converted to cysteine, which can be a source of further chemical modifications (See Scheme 1). One such useful reaction is oxidative sulfur-sulfur coupling. This reaction simply converts the cysteine back to cystine and reforms the crosslinks between proteins. This is a useful reaction for increasing the molecular weight of the gamma or alpha fraction of interest, which in turn will modify the bulk properties of the material. Increasing molecular weight influences material properties such as viscosity, dry film strength, gel strength, etc. Such reformed kerateines are referred to as meta keratins.

Meta keratins can be derived from the gamma or alpha fractions, or a combination of both. Oxidative re-crosslinking of the kerateines is affected by addition of an oxidizing agent such as peracetic acid or hydrogen peroxide. A preferred oxidizing agent is oxygen. This reaction can be accomplished simply by bubbling oxygen through the kerateine solution or by otherwise exposing the sample to air. Optimizing the molecular weight through the use of metakeratins allows formulations to be optimized for a variety of properties including viscosity, film strength and elasticity, fiber strength, and hydrolytic susceptibility. Crosslinking in air works to improve biocompatibility by providing biomaterial with a minimum of foreign ingredients.

Any suitable substrate (typically a device intended for implanting into or inserting into a human or animal subject) may be coated or treated with keratin materials or keratin derivatives as described herein, including but not limited to grafts such as vascular grafts, vascular stents, catheters, leads, pacemakers, cardioverters, valves, fasteners or ports such as heart valves, etc.

The substrate may be formed from any suitable material, including but not limited to organic polymers (including stable polymers and biodegradable or bioerodable polymers), natural materials (e.g., collagen), metals (e.g., platinum, gold, stainless steel, etc.) inorganic materials such as silicon, glass, etc., and composites thereof.

Coating of the substrate may be carried out by any suitable means, such as spray coating, dip coating, or the like. In some embodiments, steps may be taken to couple or covalently couple the keratin to the substratem such as with a silane coupling agent, if so desired. The keratin derivative may be subsequently coated with another material, and/or other materials may be co-deposited with the keratin derivative, such as one or more additional active agents, stabilizers, coatings, etc.

Another aspect of the present invention is an implantable anti-adhesive tissue barrier, comprising: a solid, physiologically acceptable substrate (typically a sheet material, including but not limited to films, and woven and non-woven sheet materials formed from organic polymers or natural materials); and a keratin derivative on the substrate. In some embodiments the keratin derivative comprises, consists of or consists essentially of basic alpha keratose, basic alpha kerateine, or combinations thereof.

The present invention is explained in greater detail in the following non-limiting Examples.

EXAMPLE 1

Crude Keratose Samples

Keratose fractions were obtained using a method based on that of Alexander and coworkers. However, the method was substantially modified to minimize hydrolysis of peptide bonds. Briefly, 50 grams of clean, dry hair that was collected from a local barber shop was reacted with 1000 mL of an aqueous solution of 2 w/v % peracetic acid (PAA) at room temperature for 12 hr. The oxidized hair was recovered using a 500 micron sieve, rinsed with copious amounts of DI water, and the excess water removed. Keratoses were extracted from the oxidized hair fibers with 1000 mL of 100 mM Trizma® base. After 3 hours, the hair was separated by sieve and the liquid neutralized by dropwise addition of hydrochloric acid (HCl). Additional keratoses were extracted from the remaining hair with two subsequent extractions using 1000 mL of 0.1 M Trizma® base and 1000 mL of DI water, respectively. Each time the hair was separated by sieve and the liquid neutralized with HCl. All three extracts were combined, centrifuged, and any residual solid material removed by filtration. The combined extract was purified by tangential flow dialysis against DI water with a 1 KDa nominal low molecular weight cutoff membrane. The solution was concentrated and lyophilized to produce a crude keratose powder.

EXAMPLE 2

Crude Kerateine Samples

Kerateine fractions were obtained using a modification of the method described by Goddard and Michaelis. Briefly, the hair was reacted with an aqueous solution of 1M TGA at 37° C. for 24 hours. The pH of the TGA solution had been adjusted to pH 10.2 by dropwise addition of saturated NaOH solution. The extract solution was filtered to remove the reduced hair fibers and retained. Additional keratin was extracted from the fibers by sequential extractions with 1000 mL of 100 mM TGA at pH 10.2 for 24 hours, 1000 mL of 10 mM TGA at pH 10.2 for 24 hours, and DI water at pH 10.2 for 24 hours. After each extraction, the solution was centrifuged, filtered, and added to the dialysis system. Eventually, all the extracts were combined and dialyzed against DI water with a 1 KDa nominal low molecular weight cutoff membrane. The solution was concentrated, titrated to pH 7, and stored at approximately 5% total protein concentration at 4° C. Alternately, the concentrated solution could be lyophilized and stored frozen and under nitrogen.

EXAMPLE 3

Ion Exchange Chromatography

Just prior to fractionation, keratose samples were re-dissolved in ultrapure water and titrated to pH 6 by addition of dilute HCl solution. Kerateine samples were titrated to pH 6 by careful addition of dilute HCl solution as well. The samples were loaded onto a 200 mL flash chromatography column containing either DEAE-Sepharose (weakly anionic) or Q-Sepharose (strongly anionic) exchange resin (50-100 mesh; Sigma-Aldrich, Milwaukee, Wis.) with gentle pressure and the flow through collected (acidic keratin). A small volume of 10 mM Trizma® base (approximately 200 mL) at pH 6 was used to completely wash through the sample. Basic keratin was eluted from the column with 100 mM tris base plus 2M NaCl at pH 12. Each sample was separately neutralized and dialyzed against DI water using tangential flow dialysis with a LMWCO of 1 KDa, concentrated by rotary evaporation, and freeze dried.

EXAMPLE 4

Evaluation of Viscosity and Red Blood Cell Aggregation

As previously described, a sample of alpha-keratose was produced, separated on a DEAE-Sepharose IEx column into acidic and basic fractions, dissolved in PBS, and the pH adjusted to 7.4. These solutions were prepared at 5 weight percent concentration and their RBC aggregation characteristics grossly evaluated with fresh whole human blood by mixing at a 1:1 ratio. Samples were taken after 20 minutes and evaluated by light microscopy. The ion exchange chromatography was highly effective at separating the aggregation phenomenon (data not shown). Basic alpha-keratose was essentially free from interactions with blood cells while the acidic alpha-keratose caused excessive aggregation.

Samples of acidic and basic alpha keratose, unfractionated alpha+gamma-kerateines, unfractionated alpha+gamma-keratose, and beta-keratose (derived from cuticle) were prepared at approximately 4 w/v % and pH 7.4 in phosphate buffered saline (PBS). Samples were tested for viscosity and red blood cell (RBC) aggregation. These results are shown in Table 1:

TABLE 1

Results of viscosity and RBC aggregation tests on keratin solutions. Fluid formulations were prepared at approximately 4 w/v % in PBS at pH 7.4 and tested with human whole blood at a ratio of 1:1.

| Sample Description | Viscosity (centipoise) | RBC Aggregation* |
|---|---|---|
| acidic alpha-keratose (1X AIEx) | 5.65 | 3 |
| acidic alpha-keratose (2X AIEx) | 19.7 | 5 |
| basic alpha-keratose | 1.57 | 2 |
| alpha + gamma-keratose (hydrolyzed) | 1.12 | 1 |
| alpha + gamma-kerateine (unfractionated) | 1.59 | 2 |

*Degree of aggregation: 1 = none, 5 = high

The foregoing is illustrative of the present invention, and is not to be construed as limiting thereof. The invention is defined by the following claims, with equivalents of the claims to be included therein.

That which is claimed is:

1. A method of producing a charged fraction of keratin, comprising:
   providing a solution comprising acidic and basic keratin, wherein said solution has a pH of between 6 and 7, and wherein said solution is provided by:
   reacting human hair with thioglycolic acid, and
   extracting said acidic and basic keratin with a solution comprising tris base;
   separating a fraction of said acidic keratin or a fraction of said basic keratin from said solution comprising said acidic and basic keratin, wherein said separating is carried out by chromatography; and
   collecting said fraction;
   to produce the charged fraction of keratin.

2. The method of claim 1, wherein said keratin comprises alpha keratin.

3. The method of claim 1, wherein said keratin comprises gamma keratin.

4. A method of producing a charged fraction of alpha keratin, comprising:
   providing a solution comprising keratin, wherein said solution is provided by:
   reacting human hair with thioglycolic acid, and
   extracting said keratin with a solution comprising tris base;
   precipitating alpha keratin from said solution comprising keratin by addition of mineral acid to a pH of approximately 4;
   separating precipitated alpha keratin from said solution comprising keratin;
   collecting the precipitated alpha keratin; and then,
   optionally, re-dissolving the alpha keratin at pH 9 and re-precipitating at pH 4 to further purify; and then,
   re-dissolving the alpha keratin to provide a purified alpha keratin solution and adjusting the pH of the purified alpha keratin solution to be between 6 and 7, wherein the purified alpha keratin solution comprises acidic and basic alpha keratin; and then,
   separating a fraction of said acidic alpha keratin or a fraction of said basic alpha keratin from said purified alpha keratin solution, wherein said separating is carried out by chromatography; and
   collecting said fraction;
   to thereby produce the charged fraction of alpha keratin.

5. The method of claim 1, wherein said keratin comprises at least 80% by weight of alpha keratin.

6. The method of claim 1, wherein said keratin comprises at least 90% by weight of alpha keratin.

* * * * *